US012751811B2

(12) United States Patent
Clarke et al.

(10) Patent No.: US 12,751,811 B2
(45) Date of Patent: Oct. 6, 2026

(54) HEART VALVE STORAGE AND SHIPPING PACKAGING

(71) Applicant: Medtronic, Inc., Minneapolis, MN (US)

(72) Inventors: David Clarke, Loughrea (IE); Joshua Hillas, Loughrea (IE); Jeffrey B. Barnell, Santa Rosa, CA (US); Christopher T. Faherty, Inis Mor (IE); Emily P. Theriot, Mandeville, LA (US)

(73) Assignee: MEDTRONIC, INC., Minneapolis, MN (US)

( * ) Notice: Subject to any disclaimer, the term of this patent is extended or adjusted under 35 U.S.C. 154(b) by 87 days.

(21) Appl. No.: 18/282,485

(22) PCT Filed: Apr. 4, 2022

(86) PCT No.: PCT/IB2022/053115

§ 371 (c)(1),
(2) Date: Sep. 15, 2023

(87) PCT Pub. No.: WO2022/214938

PCT Pub. Date: Oct. 13, 2022

(65) Prior Publication Data

US 2024/0148486 A1 May 9, 2024

Related U.S. Application Data

(60) Provisional application No. 63/171,907, filed on Apr. 7, 2021.

(51) Int. Cl.

| | |
|---|---|
| ***A61F 2/00*** | (2006.01) |
| ***A61F 2/24*** | (2006.01) |
| ***B65D 1/26*** | (2006.01) |
| ***B65D 51/00*** | (2006.01) |
| ***B65D 77/20*** | (2006.01) |

(Continued)

(52) U.S. Cl.
CPC .......... *A61F 2/0095* (2013.01); *A61F 2/2418* (2013.01); *B65D 1/26* (2013.01); *B65D 51/002* (2013.01); *B65D 77/2024* (2013.01); *B65D 81/2015* (2013.01); *B65D 81/22* (2013.01); *B65D 81/3876* (2013.01);
(Continued)

(58) Field of Classification Search
CPC ..... A61F 2/2418; A61F 2/0095; B65D 81/22; B65D 77/2024; A61B 50/30
USPC ........................................ 206/205, 438, 363
See application file for complete search history.

(56) References Cited

U.S. PATENT DOCUMENTS 4,512,471 A 4/1985 Kaster et al.
5,720,391 A * 2/1998 Dohm .................. A61F 2/0095 206/583

(Continued)

FOREIGN PATENT DOCUMENTS

EP 2659862 11/2013
JP 2006-064249 3/2006

(Continued)

OTHER PUBLICATIONS

International Search Report dated Jul. 6, 2022 in International Application No. PCT/IB2022/053115.

*Primary Examiner* — Steven A. Reynolds
(74) *Attorney, Agent, or Firm* — Wentsler LLC

(57) ABSTRACT

Packaging systems and methods for wet storage and/or shipping of prosthetic heart valve or other medical devices are disclosed.

21 Claims, 16 Drawing Sheets

(51) Int. Cl.
*B65D 81/20* (2006.01)
*B65D 81/22* (2006.01)
*B65D 81/38* (2006.01)

(52) U.S. Cl.
CPC .. *A61F 2250/0069* (2013.01); *B65D 2203/00* (2013.01); *B65D 2577/205* (2013.01)

(56) References Cited

U.S. PATENT DOCUMENTS

| | | | | |
|---|---|---|---|---|
| 6,379,740 | B1 * | 4/2002 | Rinaldi | A61F 2/0095 427/244 |
| 6,591,998 | B2 * | 7/2003 | Haynes | A61F 2/24 215/276 |
| 6,622,864 | B1 * | 9/2003 | Debbs | A61B 50/30 206/363 |
| 2012/0290079 | A1 * | 11/2012 | Murad | A61F 2/2412 623/2.17 |
| 2013/0017609 | A1 * | 1/2013 | Kansakoski | B65D 79/02 422/50 |
| 2017/0056149 | A1 * | 3/2017 | Rajpara | A61F 2/0095 |
| 2018/0206969 | A1 | 7/2018 | Liburd et al. | |
| 2020/0060816 | A1 | 2/2020 | Campbell et al. | |

FOREIGN PATENT DOCUMENTS

| | | |
|---|---|---|
| JP | 2006-273395 | 10/2006 |
| WO | 2017/085704 | 5/2017 |
| WO | 2018/204455 | 11/2018 |

* cited by examiner

HEART VALVE STORAGE AND SHIPPING PACKAGING

CROSS-REFERENCE TO RELATED APPLICATIONS

This is the National Stage under 35 U.S.C. § 371 of International Application No. PCT/IB2022/053115, filed Apr. 4, 2022, which claims the benefit of U.S. Provisional Patent Application No. 63/171,907, filed Apr. 7, 2021, the entire content of which is incorporated herein by reference.

FIELD OF INVENTION

The present disclosure relates to systems, devices and methods for packaging prosthetic heart valves or replacement heart valves and the like for storing and shipping after manufacture. More particularly, it relates to sterile barrier packaging systems for solution-sterilized prosthetic heart valves.

BACKGROUND

Prosthetic heart valves are manufactured and prepared for insertion into patients during a surgical procedure. The valves must be sterilized after manufacture and stored in a container for shipment to a hospital or surgery center. The valve is then removed from its packaging, rinsed, and prepared for placement in a patient during surgery.

A viable container for a packaged prosthetic heart valve should preserve the sterile condition of the valve and protect the valve from damage during shipment. Sterilization is critical and challenging in working with prosthetic devices. With some prosthetic heart valve packaging approaches, the valve is submerged in a sterilization solution (sometimes referred to as "wet" storage), such as a 0.2% glutaraldehyde solution. Glass jars or translucent resin jars are commonly used as the container for such packaging schemes (i.e., where the prosthetic heart valve is to remain submerged in a sterilization solution during shipment and storage) because the selected material resists reacting with the solution, is generally inexpensive, and can withstand sterilization. Conventionally, the jar container is covered and sealed with a threaded lid and silicone seal. It can at times be somewhat difficult for an end user to remove the so-assembled lid.

Moreover, additional or secondary packaging materials and the like are often employed when shipping glass (or similar material) container-packaged prosthetic heart valves, endeavoring to provide robust protection against thermal and physical damage. For example, the primary packaging (i.e., jar with threaded lid containing a prosthetic heart valve and sterilization solution) can be placed within a formed cushioning structure (e.g., foam) and loaded into a paperboard carton to provide a packaged unit. Additional thermal and physical protection is typically utilized when shipping the packaged unit. For example, multiple packaged units are typically placed into an insulated shipping container (e.g., outer cardboard box with foam panels or foil lining for thermal insulation, and one or more refrigerant-type items (e.g., refrigerant phase change gel packs) for cooling) when shipped from the manufacturer to a distribution center. These and other steps can be important to ensure that the prosthetic heart valve stays within a specific temperature range. A protective insulated shipping container may not be available for delivery of a packaged unit from the distribution center to an end user.

SUMMARY

The inventors of the present disclosure recognized that a need exists for improved packaging systems and methods for storage and/or shipment prosthetic heart valves and similar products.

Some aspects of the present disclosure relate to packaging systems for storing a prosthetic heart valve in a sterilization solution that include a cup and a lid. The cup is sized and shaped to contain the prosthetic heart valve and a volume of sterilization solution sufficient, for example, for submerging the prosthetic heart valve. The lid is configured for a securement to the cup in a manner that does not include or entail a threaded connection. For example, the lid can be a thin foil or film that is sealed (e.g., heat sealed) to the cup. With these non-limiting embodiments, the lid can be removed from the cup for accessing the prosthetic heart valve by peeling the lid away from the cup. In other examples, the cup and the lid can be akin to a conventional consumable product can (e.g., soup can) in which a metal lid can be pulled away from the cup along a score line. In yet other embodiments, the prosthetic heart valve and sterilization solution are held by a protective frame and contained within a flexible pouch with an easy opening, sealed end. Regardless, the packaging systems of the present disclosure can overcome concerns associated with convention packaging, such as the sterilization solution crystallizing between a threaded interface between glass jar and lid.

In some embodiments, the packaging systems can further include a vacuum flask and corresponding cap. For example, the prosthetic heart valve and sterilization solution can be sealed and contained within the cup and lid to provide a wet packaged prosthetic heart valve that in turn can be placed within the vacuum flask and covered by the cap. The vacuum flask and cap combine to provide thermal and physical protection for the wet packaged prosthetic heart valve, and is well suited for expected shipping and storage conditions. In related embodiments, a temperature indicator device can be provided with the flask and cap, and include a temperature sensor located in close proximity to the wet packaged prosthetic heart valve (e.g., the temperature sensor is located on the lid and thus inside of the vacuum flask/cap). With these and related embodiments, the temperature indicator device provides a meaningful representation of temperature conditions directly experienced by the prosthetic heart valve/sterilization solution. In yet other embodiments, the temperature indicator device include a display component that is visible from an exterior of the cap, providing a viewer with information indicative of the prosthetic heart valve temperature conditions while stored (and shipped) within the flask.

DETAILED DESCRIPTION

Aspects of the disclosure are directed to packaging systems for storage of a prosthetic heart valve in a sterilization solution, and resultant wet packaged prosthetic heart valves. In some embodiments, the packaging systems of the present disclosure promote consistent, easy opening by an end user for accessing the stored prosthetic heart valve. In some embodiments, the packaging systems of the present disclosure can provide one or more additional features, for example thermal and physical protection appropriate for shipping, storing, and validation of the packaged prosthetic heart valve. In some embodiments, the packaging systems of the present disclosure are useful with and can accommodate different sizes and/or styles of prosthetic heart valves, affording a manufacturer the ability to employ a single packaging scheme with multiple different products. The packaging systems and methods of the present disclosure can be useful with items other than prosthetic heart valves, for example other medical device products benefiting from storage in a liquid solution. Further, the packaging systems and methods of the present disclosure can be useful for the storage and/or shipping of dry products, such as a "dry" stored prosthetic heart valve; thus, in alternative embodiments, the packaging systems can disclosed below can be utilized without a sterilization solution or other liquid.

As a point of reference, the packaging systems and methods of the present disclosure are useful with a plethora of differently-configured prosthetic heart valves. For example, the packaging systems and methods of the present disclosure can be useful with a prosthetic heart valve designed or configured to replace an aortic valve, a mitral valve, a tricuspid valve, or a pulmonic valve. Similarly, the packaging systems and methods of the present disclosure can be useful with a prosthetic heart valve designed or configured for transcatheter implantation or open-heart surgical implantation. Thus, to the extent the drawings might implicate a particular prosthetic heart valve design, the present disclosure is in no way limited. The prosthetic heart valves envisioned by the present disclosure more generally entail a structure (e.g., a stent or frame) supporting one or more leaflets (e.g., tissue or synthetic).

Figure 1:
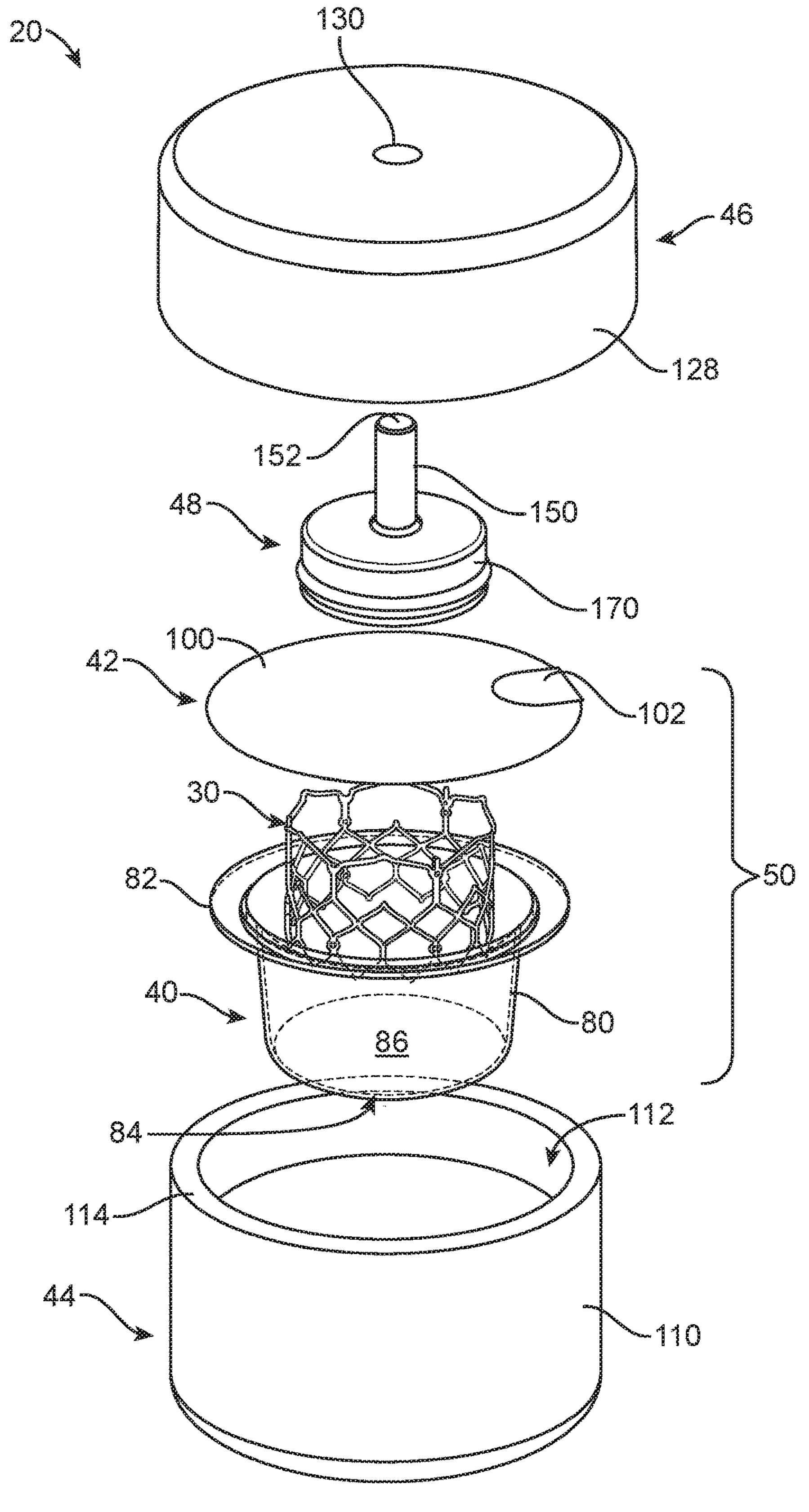
FIG. 1 is a perspective, exploded view of a packaging system in accordance with principles of the present disclosure along with a prosthetic heart valve to be stored using the packing system.

One embodiment of a packaging system 20 for storage of a prosthetic heart valve 30 in accordance with principles of the present disclosure is shown in FIG. 1. The packaging system 20 includes a cup 40, a lid 42, a vacuum flask 44, a cap 46, and an optional temperature indicator device 48. Details on the various components are provided below. In general terms, however, the cup 40 and lid 42 combine to serve as primary packaging, containing the prosthetic heart valve 30 and a sterilization solution (not shown), such as a glutaraldehyde solution, in a sealed environment. A wet packaged prosthetic heart valve 50 (referenced generally) is defined as the prosthetic heart valve 30 and sterilization solution sealed within the cup 40 and the lid 42 (e.g., a "wet packaged prosthetic heart valve" can be in reference to a prosthetic heart valve and sterilization solution secured within primary packaging, and the prosthetic heart valve is immediately or directly accessible upon opening the primary packaging). The vacuum flask 44 is configured to receive the wet packaged prosthetic heart valve 50, with the flask 44 and the cap 46 combining to provide secondary or outer packaging 60 (best identified in FIG. 2). Upon assembly of the cap 46 to the flask 44, the outer packaging 60 provides robust thermal and physical protection for the wet packaged prosthetic heart valve 50, and in particular the prosthetic heart valve 30. With additional reference to FIG. 2, a prosthetic heart valve packaged unit 70 is defined as the wet packaged heart valve 50 contained within the outer packaging 60 (e.g., a "prosthetic heart valve packaged unit" can be in reference to a wet packaged prosthetic heart valve secured within an outer container, and the prosthetic heart valve is not immediately or directly accessible upon opening the outer container).

The prosthetic heart valve packaged unit 70 is well suited for all stages of shipment from a manufacturer to an end user. Optionally, the prosthetic heart valve packaged unit 70 can be placed in a labeled outer carton prior to shipment; in some embodiments, however, no additional or secondary thermal insulation packaging is required. To access the wet packaged prosthetic heart valve 50, the cap 46 is readily removable from the flask 44. To then access the prosthetic heart valve 30, the lid 42 is easily removed from the cup 42. The optional temperature indicator device 48 can be contained within the outer packaging 60, sensing temperature conditions experienced by the wet packaged prosthetic heart valve 50, and thus by the prosthetic heart valve 30, while maintained within the outer packaging 60. An end user can thus quickly and confidently verify implantability of the prosthetic heart valve 30.

Figure 4:
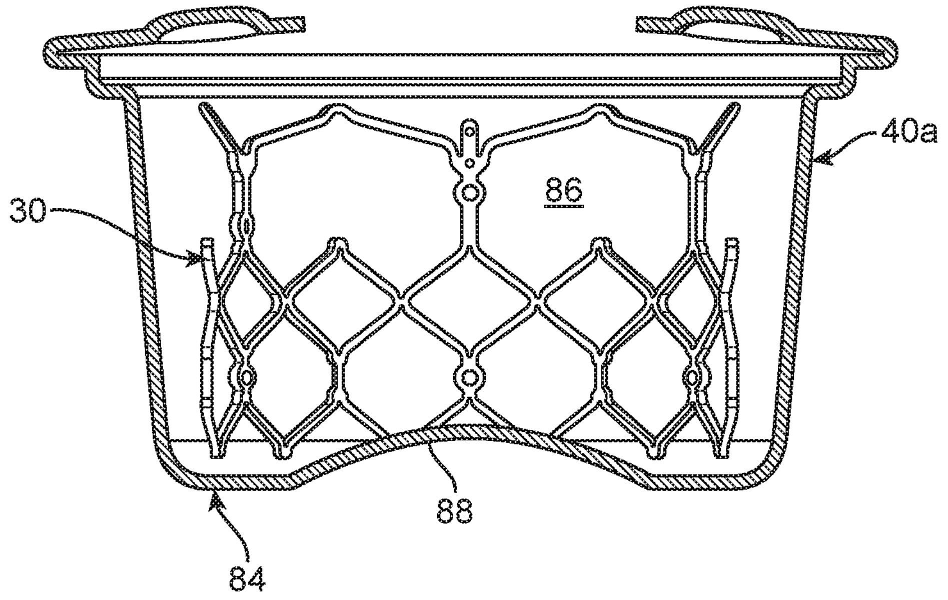
FIG. 4 is a cross-sectional view of a cup useful with the packaging system of FIG. 1 loaded with a prosthetic heart valve.

The cup 40 can assume various forms appropriate for containing the prosthetic heart valve 30 and a volume of sterilizing solution (or other liquid), as well as facilitating assembly of the lid 42. For example, with the non-limiting example of FIG. 1, the cup 40 includes or defines a cup body 80 and a rim 82. The cup body 80 extends from a closed end 84 (referenced generally) to the rim 82. An interior region 86 of the cup body 80 is open at the rim 82, and is sized and shaped to receive an entirety of the prosthetic heart valve 30 in a configuration intended by the manufacturer for storage prior to implant. In some embodiments, the interior region 86 is sized and shaped to accommodate different sizes of a particular style of prosthetic heart valve (e.g., some manufacturers provide a particularly-designed prosthetic heart valve in two or more sized). For example, FIGS. 3A-3D illustrate another cup 40*a* useful with the packaging system 20 (FIG. 1) and accommodating different sizes of the same style prosthetic heart valve 30*a*-30*d* (e.g., the prosthetic heart valves 30*a*-30*d* are the same design/style, but progressively smaller from FIG. 3A to FIG. 3D). Regardless, and returning to FIG. 1, the interior region 86 can be sized and shaped to be slightly larger than a size/shape of the largest prosthetic heart valve intended to be packaged. For example, where the prosthetic heart valve 30 is generally cylindrical in shape, a geometry of the interior region 86 can be akin to a right cylinder, having a diameter approximating a diameter of the prosthetic heart valve 30 and a height slightly larger than a height of the prosthetic heart valve 30. These and other attributes can serve to minimize an overall footprint of the cup body 80 and a volume of the sterilization solution required to submerge the prosthetic heart valve 30 as compared to some conventional designs in which the prosthetic heart valve is stored/shipped in a standard-sized glass jar that is typically much larger than the prosthetic heart valve 30. Other features can optionally be incorporated into the cup body 80 to further reduce the requisite volume of sterilization solution. For example, and as shown for the cup 40*a* in FIG. 4, an inward protrusion 88 can be defined at the closed end 84 that reduces a volume of the interior region 86.

Returning to FIG. 1, the cup 40 can be formed from a variety of materials compatible with both the prosthetic heart valve 30 and the solution (e.g., sterilization solution) to be contained in the cup 40. For example, where the solution is a glutaraldehyde solution, the material selected for the cup 40 will not degrade in the presence of the glutaraldehyde solution. Further, the material of the cup 40 is desirably selected to establish a sterile barrier for the interior region 86. In some embodiments, at least the cup body 80 is formed to be transparent or substantially transparent (i.e., with 10% of truly transparent) to permit viewing of the prosthetic heart valve 30 when disposed in the interior region 86. For example, in some non-limiting embodiments, the cup 40 is a thermoformed plastic structure formed of a transparent or substantially transparent resin such as clear polypropylene, a copolyester material available from Eastman Chemical Co. under the tradename Tritan™, etc. Other materials and/or manufacturing techniques (e.g., blow molding, injection molding, etc.) are also acceptable.

Figure 5:
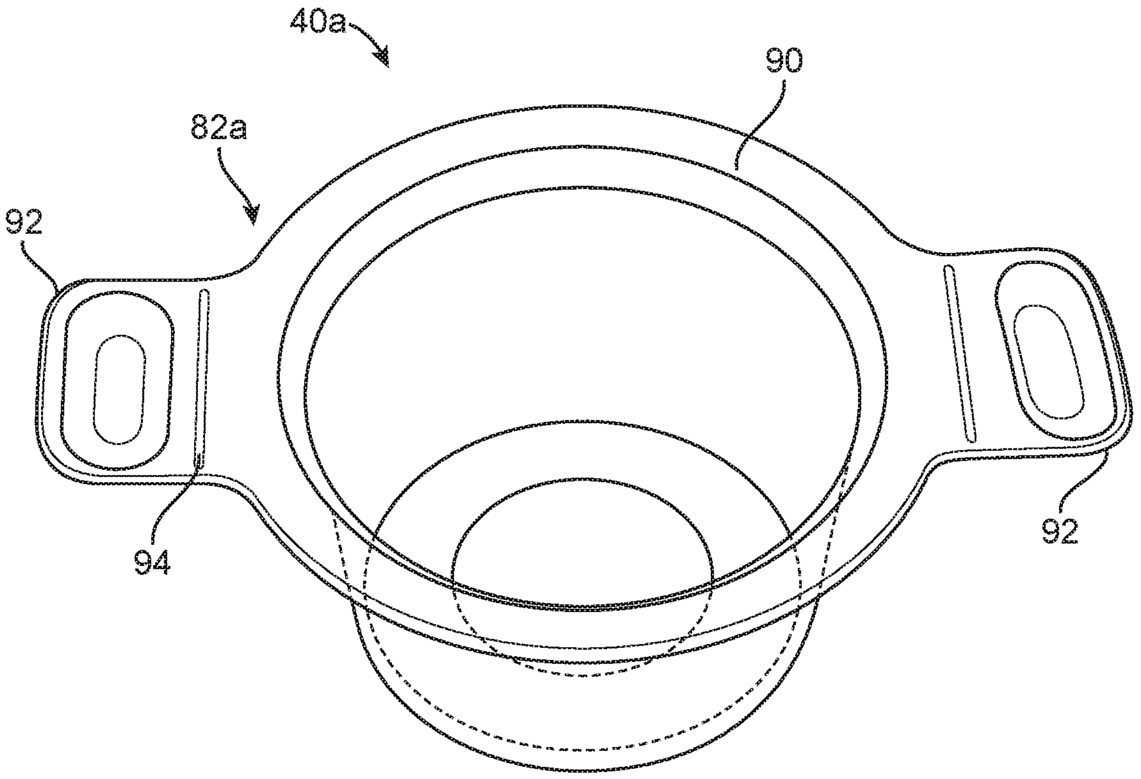
FIG. 5 is a perspective view of a cup useful with the packaging system of FIG. 1.

The rim 82 is sized and shaped to promote attachment of the lid 42. For example, where the lid 42 is to be heat sealed to the rim 82, the rim 82 can form or define a relatively flat receiving surface. The rim 82 can be integrally formed with the cup body 80, or can be separately formed and subsequently attached. In some embodiments, where the cup body 80 has a cylindrical shape, the rim 82 can be formed to have a ring or ring like shape. Other configurations are also acceptable. For example, while the rim 82 is shown in FIG. 1 as being a ring, one or more additional features can be provided. For example, with the cup 40*a* as shown in FIG. 5, a rim 82*a* is provided and includes a rim body 90 and one or more tabs 92. The rim body 90 provides a surface for receiving the lid 42 (FIG. 1). The tab(s) 92 extend radially outward from the rim body 90. A fold line 94 is formed and about which the corresponding tab 92 can pivot relative to the rim body 90. With this construction, the tab(s) 92 can be folded upwardly relative to the rim body 90 during insertion into the vacuum flask 44 (FIG. 1), providing a convenient surface for grasping by a user to remove the cup 40*a* from the vacuum flask 44 as described in greater detail below.

Returning to FIG. 1, the lid 42 is sized and shaped in accordance with cup 40, and in particular the rim 82, for assembly thereto. In some embodiments, the lid 42 can be a thin film or foil-type body, formed of a material conducive to sealing to the rim 82, that can provide a hermetically sealed, sterile barrier to the interior region 86, and that is compatible with the solution (e.g., sterilization solution) to be contained in the cup 40. For example, where the solution is a glutaraldehyde solution, the material selected for the lid 42 will not degrade in the presence of the glutaraldehyde solution. For example, the lid 42 can be a film or foil that is sealed or otherwise attached to the rim 82 by conventional heat sealing techniques, such as materials and seal manufacturing approaches used with single serving coffee creamer packaging, single serving yogurt packaging, etc. In some embodiments, the lid 42 can provide or include one or more features that facilitate removal from the cup 40 by a user. For example, the lid 42 can form or provide a lid body 100 and a pull tab 102. The lid body 100 is sized and shaped in accordance with a size and shape of the rim 82. The pull tab 102 extends from the lid body 100 and provides a convenient surface for grasping by a user when removing the lid 42 from the cup 40.

Upon final assembly, the cup 40 and the lid 42 provide a secure, long term, sterile barrier for the contained prosthetic heart valve 30 and the sterilization solution. When a user desires to access the prosthetic heart valve 30, the lid 42 is readily removed from the cup 40, for example by pulling on the pull tab 102 to peel the lid 42 off of the rim 82. In this regard, removal of a heat sealed, foil or film from a thermoformed container (such as the cup 40) is well understood by most users. Moreover, the heat sealed format of the lid 42 to the rim 80 is not susceptible to ingress or deterioration by most, if not all, sterilization or other solutions contained with the prosthetic heart valve 30. Thus, for example, a glutaraldehyde solution will not impede or otherwise negatively affect ease of removal, in contrast to conventional glass jar/threaded lid wet prosthetic heart valve packaging (in which the glutaraldehyde solution my sometimes seep in between the threads and crystalize to essentially bond the threaded lid to the jar).

The vacuum flask 44 can assume various forms for receiving the wet packaged prosthetic heart valve 50. For example, the vacuum flask 44 can be a metal-walled (e.g., stainless steel or the like) vacuum-insulated flask. In general terms, vacuum-insulated flasks are known in the art, and are an insulated storage vessel consisting of two flasks, placed on within the other and joined at the neck. The space between the two flasks is at least partially evacuated, and the resulting near-vacuum substantially prevents heat transfer to or from the contents of the flask by either conduction or convection. The contents of a vacuum flask may thus remain either hotter or colder than the flask's surrounding environment for an extended period of time.

Figure 6:
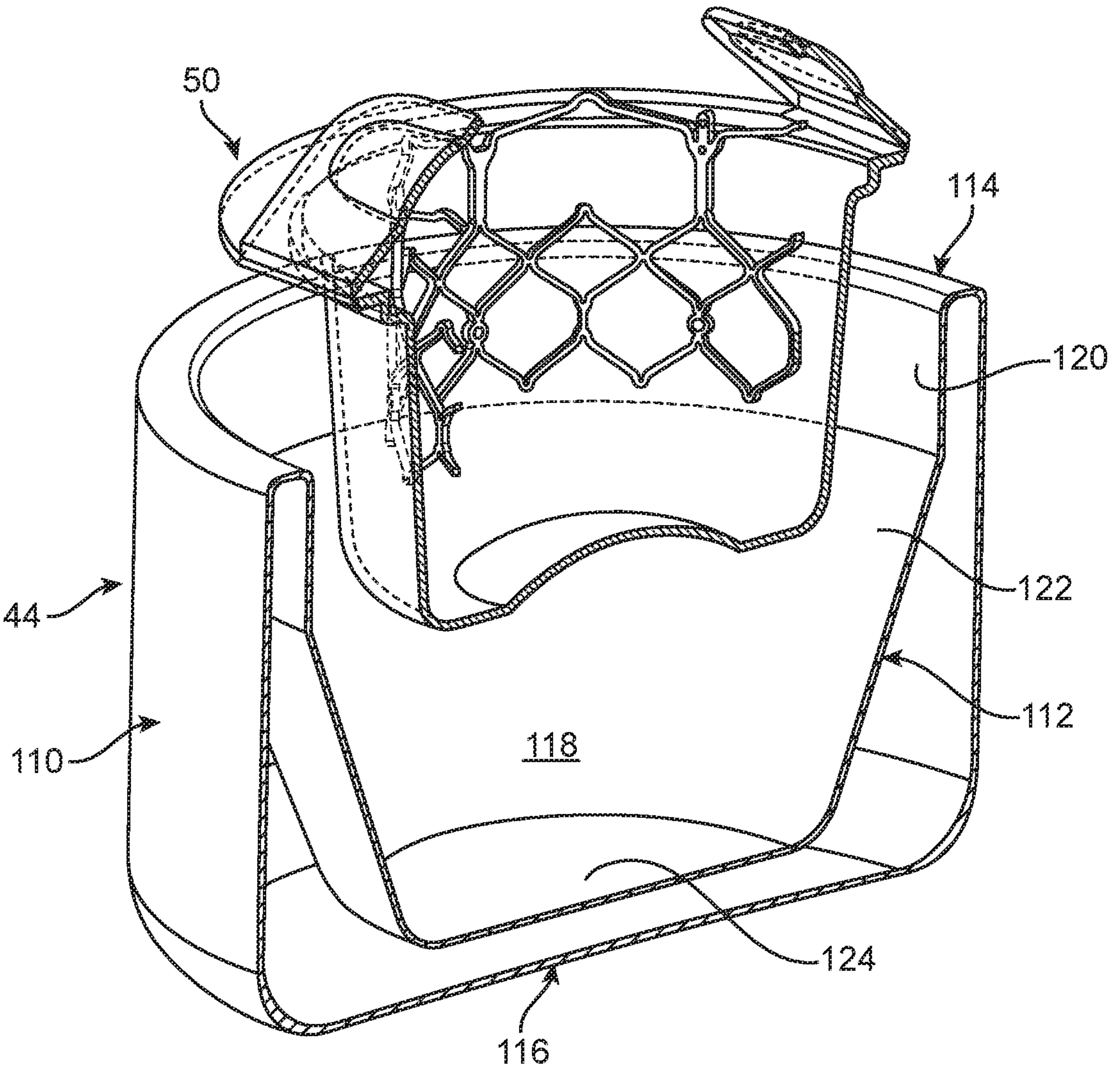
FIG. 6 is a perspective, cross-sectional view of a vacuum flask useful with the packaging system of FIG. 1 and illustrating a wet packaged prosthetic heart valve being placed into the vacuum flask.
Figure 7:
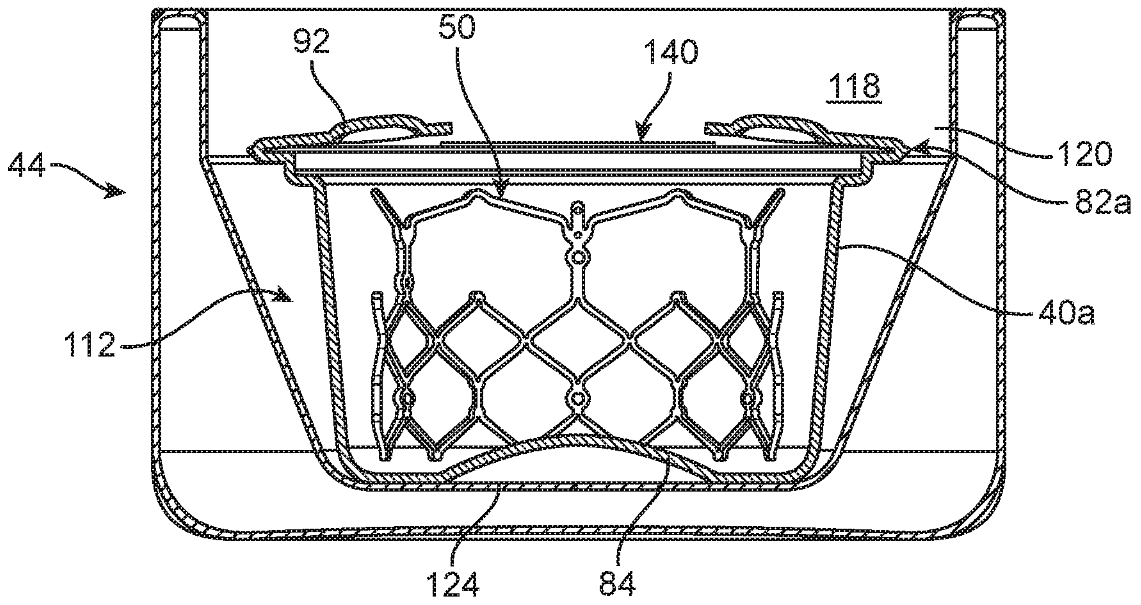
FIG. 7 is a cross-sectional view of the wet packaged prosthetic heart valve placed into the vacuum flask of FIG. 6.

With this general construction in mind, the vacuum flask 44 forms or defines an external wall 110, an internal wall 112, and a neck 114. With additional reference to FIG. 6, the external wall 110 can have a generally cylindrical shape in extension from a bottom 116 to the neck 114. The internal wall 112 defines a receptacle zone 118 that is sized and shaped to receive the wet packaged prosthetic heart valve 50, with the receptacle zone 118 be open to or accessible at the neck 114. For example, in some embodiments, the internal wall 112 can be formed to define a leading region 120 and a trailing region 122. The leading region 120 extends from the neck 114 and has a generally cylindrical shape and/or uniform diameter. The trailing region 122 extends from the leading region 120 to a base 124, and forms the receptacle zone 118 to have a generally tapering diameter. Other shapes or geometries are also acceptable. As best shown in FIG. 7, a diameter of the base 124 generally corresponds with a diameter of the closed end 84 of the cup 40*a*; with these and similar constructions, the cup 40*a* nests against the internal wall 112 at or near the base 124 to limit overt, side-to-side movement of the wet packaged prosthetic heart valve 50 upon placement into the receptacle zone 118. A diameter of the receptacle zone 118 at the leading region 120 generally corresponds with (e.g., is slightly larger than) a diameter or other major outer dimension of the cup 40*a* in a region of the rim 82*a*. For example, and as further reflected by FIG. 7, a diameter of the leading region 120 is slightly larger than an outer dimeter of the rim 82*a* (with the optional tabs 92 having been folded inwardly). With these and similar embodiments, the tabs 92 exhibit a natural, outward bias, and will pivot toward and bear against the internal wall, thereby further stabilizing the wet packaged prosthetic heart valve 50 within the receptacle zone 118. Other bodies or mechanism can optionally be provided that can stabilize the wet packaged prosthetic heart valve 50 within the receptacle zone 118. Regardless, a height of the receptacle zone 118 is selected to be at least slightly greater than a height of the wet packaged prosthetic heart valve 50.

Returning to FIG. 1, the cap 46 can assume various forms suited for releasable assembly to the vacuum flask 44, and can exhibit thermal insulative properties. For example, in some embodiments, the cap 46 is formed of a thermally insulating material, such as polyurethane foam or similar material. Other materials are also acceptable. The cap 46 (and the vacuum flask 44) can be configured for assembly in a wide variety of manners. With the non-limiting example of FIG. 1 in which the cap 46 is formed of a foam or foam-like material, a shoulder 128 of the cap 46 can have an inner diameter approximating (e.g., slightly smaller than) a diameter of the external wall 110 of the vacuum flask 44, allowing the cap 46 to be robustly connected to the vacuum flask 44 by a simple compression or friction-type fit.

The cap 46 can optionally include one or more additional features, for example that promote an interface with the optional temperature indicator device 48. For example, the cap 46 can include or define a viewing port 130 and/or indicia relating to temperature as described in greater detail below.

Where provided, the optional temperature indicator device 48 can take various forms that sense temperature and generate a display relating to temperature. For example, the temperature indicator device 48 can include a thermal sensor/indicator (hidden in FIG. 1, but identified, for example, in FIG. 7 at 140), such as a chemical temperature sensor/indicator label or sticker as is known in the art. In general terms, the thermal sensor/indicator 140 is configured to change colors when exposed to a temperature outside of a predetermined window (e.g., a "go or no go" type temperature indicating label). In some embodiments, the thermal sensor/indicator 140 is located directly on the wet packaged prosthetic heart valve 50. For example, in some non-limiting examples, the thermal sensor/indicator 140 is applied or placed onto the lid 44, or in highly close proximity to the lid 44 (e.g., the thermal sensor/indicator 140 can be carried by a thin sheet that in turn is placed on the lid 44). With these and related embodiments, the thermal sensor/indicator 140 will more closely sense temperatures being experienced by the wet packaged prosthetic heart valve 50, and thus by the prosthetic heart valve 30. This feature beneficially provides a more accurate indication of the prosthetic heart valve's suitability for implantation (e.g., the prosthetic heart valve 30 has or has not been exposed to thermal conditions outside of the predetermined window during shipping). In contrast, conventional prosthetic heart valve packaging for shipment techniques typically locates a temperature monitoring device away from the primary packaging (e.g., separated from the jar by packaging foam/air); under these circumstances, areas away from the prosthetic heart valve can experience thermal conditions causing the temperature monitoring device to trigger a warning while the prosthetic heart valve itself has not been subjected to those same thermal conditions. Thus, by locating the thermal sensor/indicator 140 at or on the wet packaged prosthetic heart valve 50, the thermal sensor/indicator 140 measures the temperature of the liquid surrounding the prosthetic heart valve 30, providing a more accurate indication of suitability of implantation and reducing instances of incorrectly rejected product.

Figure 2:
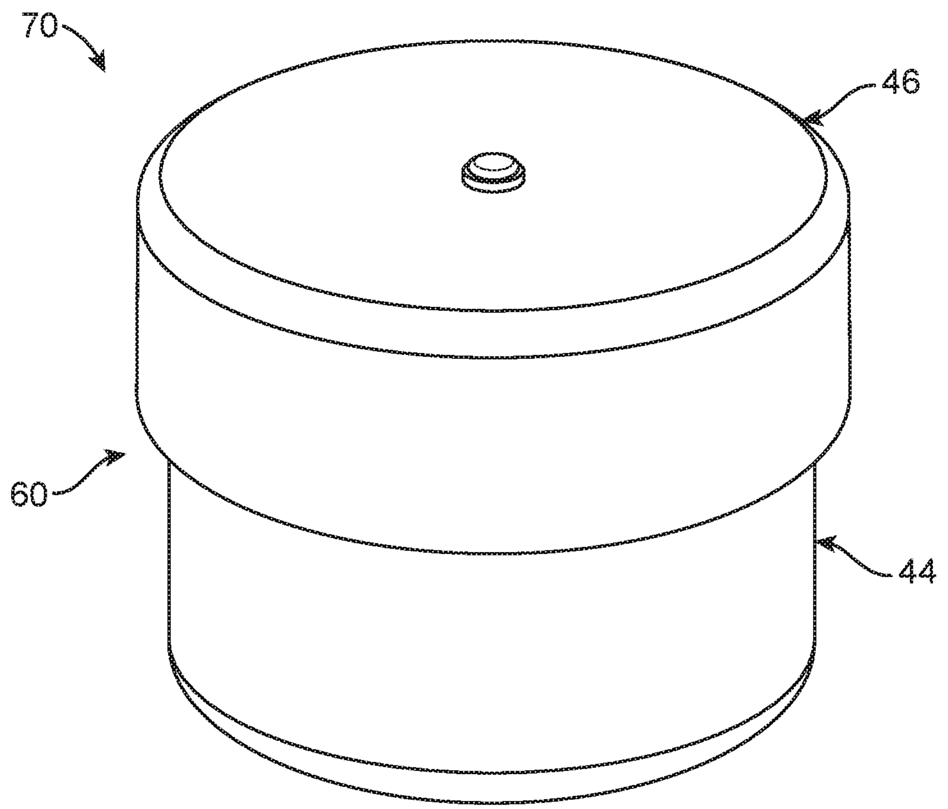
FIG. 2 is a perspective view of the packaging system of FIG. 1 upon final assembly.
Figure 3A:
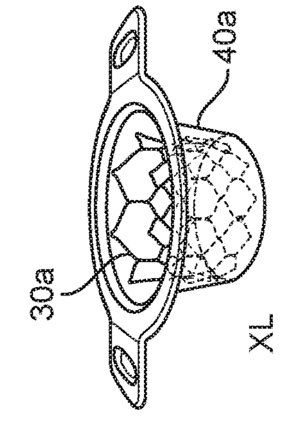
FIGS. 3A-3D are perspective views of a cup useful with the packaging system of FIG. 1 along with a differently-sized prosthetic heart valve placed in the cup.
Figure 3B:
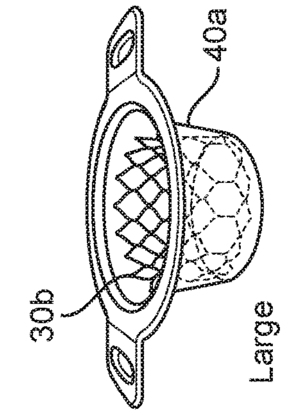
Figure 3C:
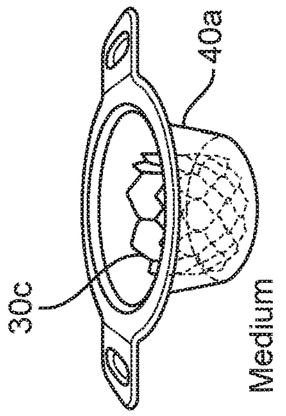
Figure 3D:
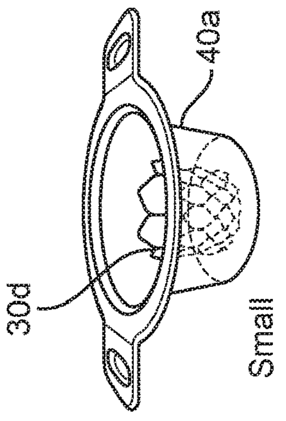
Figure 8:
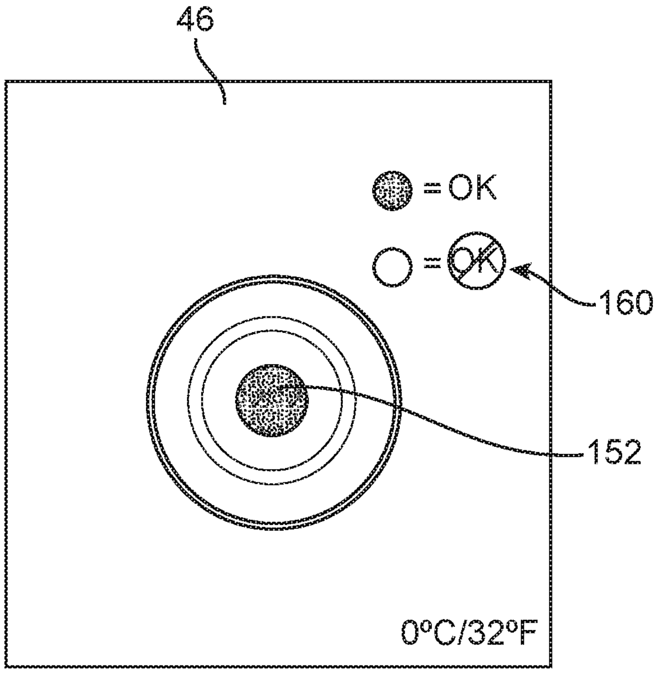
FIG. 8 is an enlarged top view of a portion of a cap useful with the packaging system of FIG. 1.

In some embodiments in which the thermal sensor/indicator 140 (FIG. 7) is or includes a temperature indicating label or the like and is located on or in close proximity to the lid 44, the temperature indicator device 48 can include one or more additional components for conveying thermal-related information to a user. For example, a light pipe or light guide 150 can be provided. The light pipe 150 can be of a type known to one of ordinary skill, arranged to receive and transfer light generated by the thermal sensor/indicator 140. For example, where the thermal sensor/indicator 140 is formatted to generate or emit visible light at predetermined wavelengths/colors that correspond with predetermined temperature conditions, a receiving end (hidden in FIG. 1) of the light pipe 150 is arranged in close proximity to the source of the so-emitted light at the thermal sensor/indicator 140. An emitting end 152 of the light pipe 150 is arranged to display the transferred light, for example to a user viewing the prosthetic heart valve packaged unit 70 (FIG. 2). In some non-limiting examples, the emitting end 152 of the light pipe 150 is disposed in the viewing port 130 of the cap 46 and is thus visible external the cap 46. In other words, the thermal sensor/indicator 140 can be located within the vacuum flask 44/cap 46, and the light (or other thermal indication) generated by the thermal sensor/indicator 140 can be viewed by a user without first removing the cap 46. In this regard, the cap 46 can optionally include or provide indicia that better explains to a viewer a meaning of the displayed color. One non-limiting example of possible indicia 160 formed on the cap 46 as shown in FIG. 8, along with the emitting end 152 of the light pipe 150 (FIG. 1). As shown, the indicia 160 can convey to a viewer a meaning of the color or light at the emitting end 152 (e.g., conveying to a user whether the displayed color indicates that thermal conditions experienced by the prosthetic heart valve 30 (FIG. 1) are or are not within an acceptable range).

Returning to FIG. 1, the temperature indicator device 48 can assume other forms or formats that promote sensing and displaying of thermal conditions or information that may or may not include the light pipe 150. In some non-limiting embodiments, the temperature indicator device 48 can alternatively include a digital-type temperature sensing and logging unit 170. The temperature sensing and logging unit 160 can be of a type known in the art, and is generally configured to sense and record temperature over time (e.g., a lifespan on the order of seven years). The sensing and logging unit 170 can include a temperature sensor (hidden) and is arranged such that upon final assembly, the temperature sensor is located in close proximity to the wet packaged prosthetic heart valve 50 for the reasons described above. The temperature sensing and logging unit 170 can further be programmed to emit a predetermined color of light (e.g., via an LED carried by the temperature sensing and logging unit 170) corresponding with a predetermined temperature window. For example, the temperature sensing and logging unit 170 can be programmed to emit a first color of light (e.g., green) when the sensed temperature is within a predetermined window, and emit a second color of light (e.g., red) when the sensed temperature is outside of the predetermined window; further programming can include the temperature sensing and logging unit 170 maintaining to the second color of light once "out of window" temperature conditions have been sensed, regardless of sensed future conditions (e.g., the temperature sensing and logging unit 160 will continually emit the second color/red even if it is later determined that the sensed temperature is subsequently within the predetermined window). With these and similar embodiments, a recorded history of thermal events associated with the wet packaged prosthetic heart valve 50 is available for review (e.g., by the valve manufacturer in the event the wet packaged prosthetic heart valve 50 is returned).

Figure 9A:
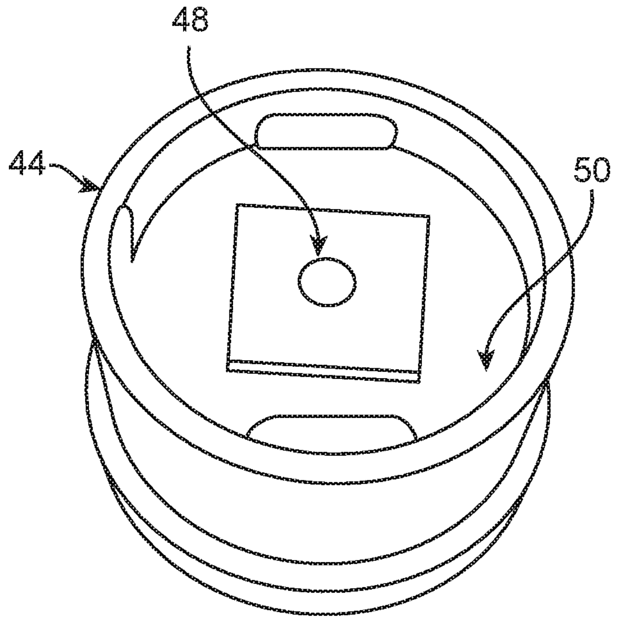
FIGS. 9A and 9B illustrate assembly of the packaging system of FIG. 1.
Figure 9B:
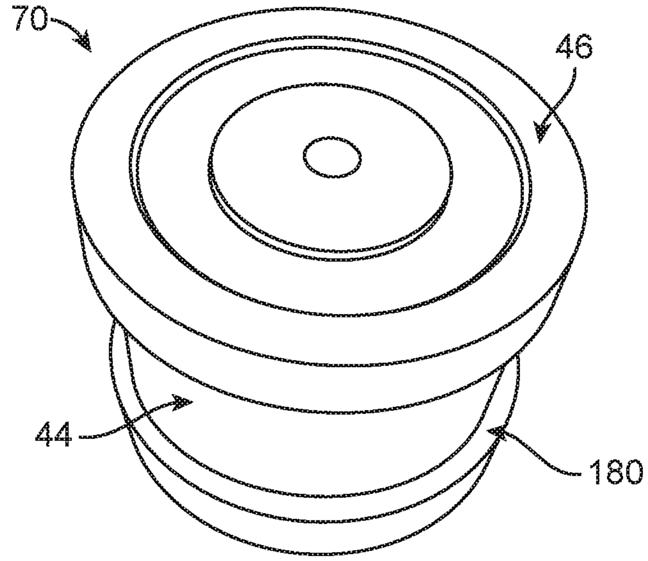

During use, the wet packaged prosthetic heart valve 50 can be prepared by the valve manufacturer by disposing the prosthetic heart valve 30 and sterilization solution in the cup 40, followed by hermetically sealing the lid 42 over the cup 40. The wet packaged prosthetic heart valve 50 can then be placed within the vacuum flask 44. Where provided, the temperature indicator device 48 can be placed onto the wet packaged prosthetic heart valve 50 as shown, for example, in FIG. 9A. The cap 46 is then assembled to the vacuum flask 44, resulting in the prosthetic heart valve packaged unit 70 of FIG. 2. In some embodiments, and as shown in FIG. 9B, a bottom 180 can be provided and assembled to the vacuum flask 44 opposite the cap 46. The bottom 180 can be formed of an insulative material similar to the cap 46, and can have similar dimensions (e.g., outer diameter) to provide the prosthetic heart valve packaged unit 70 with a more uniform footprint or shape at both ends thereof.

Returning to FIGS. 1 and 2, the prosthetic heart valve packaged unit 70 can optionally then be packaged or placed in a paperboard box, carton, etc., along with, for example, documentation, labels and instructions for use. Under these and similar packaging options, the paperboard box can include a viewing window through with the thermal display of the prosthetic heart valve packaged unit 70 is visible. The prosthetic heart valve packaged unit 70 can then be shipped to a distribution center and/or end user in any desired fashion. The vacuum flask 44 and the cap 46 provide constant protection against physical damage and temperature extremes; no additional, secondary insulated packaging is required. Returning to FIG. 1, upon receipt, the end user can immediately and accurately verify whether or not the prosthetic heart valve 30 has been exposed to temperature conditions outside of predetermined limits prior to removing the cap 46 via the temperature indicator device 48 in some embodiments. Where the user validates acceptable temperature conditions, the prosthetic heart valve 30 is easily removed from the cup 40 by simply peeling back the lid 42.

In some situations, an end user may decide to return the wet packaged prosthetic heart valve 50 (e.g., when apprised of possible temperature-related concerns). Under these and similar circumstances, the end user can simply re-secure the wet packaged prosthetic heart valve 50 within the vacuum flask 44 and the cap 46 for shipping back to the manufacturer. Unlike conventional prosthetic heart valve packaging techniques in which an end user does not have insulative packaging available for return shipping a delivered wet packaged prosthetic heart valve, the vacuum flask 44/cap 46 will provide requisite thermal and physical protection to the wet packaged prosthetic heart valve 50 throughout the return shipping process, affording the manufacturer the ability to confidently consider re-use of the wet packaged prosthetic heart valve 50 in the event of an incorrect end user rejection decision.

In yet other embodiments, a cover can be applied to the wet packaged prosthetic heart valve 50, akin, for example, to the cap described below with respect to the embodiment of FIGS. 10-12. The cover can be configured for snap fit attachment to the cup 40 or other component, serving to protect the lid 42. Presence of the cover or similar component can eliminate the need for secondary packaging (e.g., a shelf carton), with labels and other identifying information being applied, for example, directly onto the cup 40, the lid 42, and/or the cover.

Figure 10:
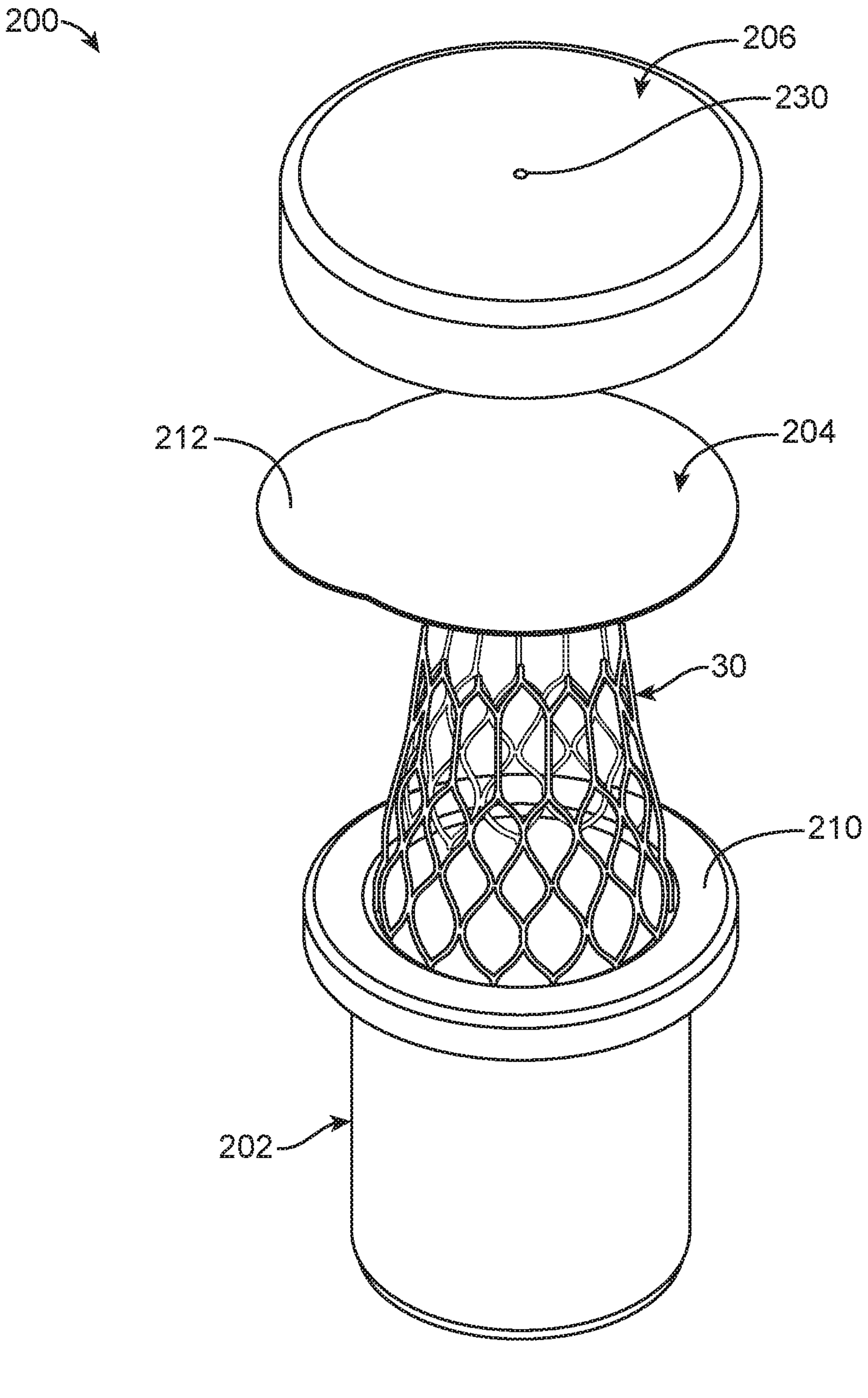
FIG. 10 is a perspective, exploded view of another packaging system in accordance with principles of the present disclosure along with a prosthetic heart valve to be stored in the packaging system.

Another embodiment of a packaging system 200 for storage of the prosthetic heart valve 30 in accordance with principles of the present disclosure is shown in FIG. 10. The packaging system includes a cup or container 202, a lid 204, and an optional cap 206. The cup 202 is sized and shaped to receive the prosthetic heart valve 30 and a volume of sterilization solution (not shown) sufficient to maintain the prosthetic heart valve 30 within the cup 202 (e.g., glutaraldehyde solution). The cup 202 can be formed of a material that is compatible with the prosthetic heart valve 30 and the sterilization solution, and in some embodiments can be transparent or substantially transparent (e.g., glass, polymer resin, etc.). A rim 210 is formed at an open end of the cup 202. The lid 204 is a flexible sheet or membrane formed of a material providing a sterile barrier for the prosthetic heart valve 30 and the sterilization solution (e.g., the lid 204 is configured to serve as a moisture and oxygen barrier). Further, a material of the lid 204 is selected to be appropriate for sealed attachment to the rim 210 using conventional sealing techniques. For example, the lid 204 can be a flexible foil, a flexible foil-like material, or plastic film, such as a type commonly used with packaging of various consumable products such as dairy products, yogurt, medicine tablets, etc. In some embodiments, the lid 204 can form a tab 212 or similar structure that facilitated removal from the cup 202 by an end user.

Figure 11:
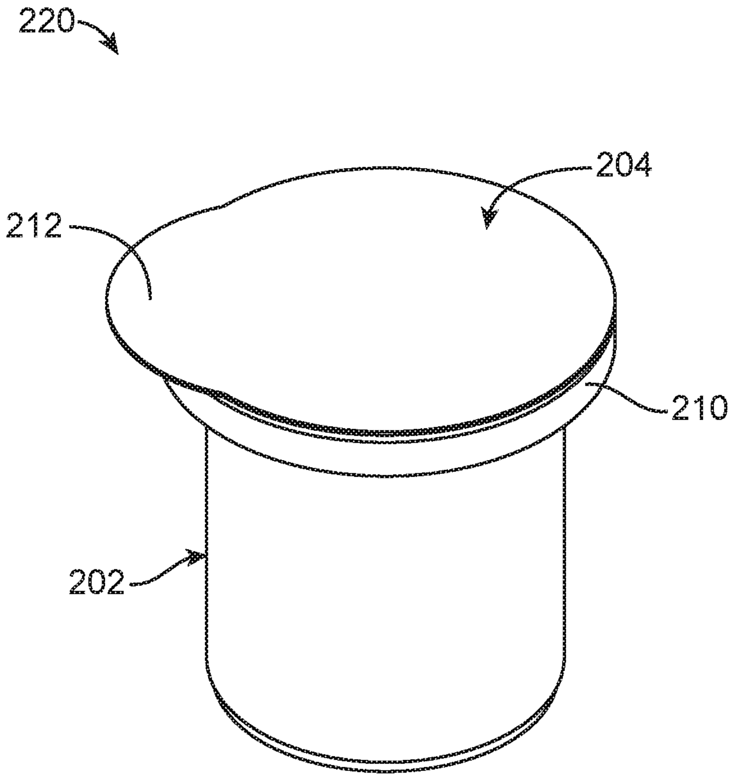
FIG. 11 is a perspective view of wet packaged prosthetic heart valve provided by the packaging system of FIG. 10.

Sealed attachment of the lid 204 to the cup 202 is shown in FIG. 11. The state of FIG. 11 (in which the prosthetic heart valve 30 (FIG. 10) and the sterilization solution (hidden) are located within the cup 202) can be considered a wet packaged prosthetic heart valve 220. To access the prosthetic heart valve 30, a user peels back the lid 204 by hand (e.g., while grasping the tab 212), breaking the seal between the lid 204 and the rim 210. Once at least partially removed/peeled away from the rim 210, the lid 204 cannot be re sealed to the cup 202 by the end user, thus providing tamper evidence. Moreover, the sealed format of the lid 204 to the rim 210 is not susceptible to ingress or deterioration by most, if not all, sterilization or other solutions contained with the prosthetic heart valve 30. Thus, for example, a glutaraldehyde solution will not impede or otherwise negatively affect ease of removal of the lid 204, in contrast to conventional glass jar/threaded lid wet prosthetic heart valve packaging (in which the glutaraldehyde solution may sometimes seep in between the threads and crystalize to essentially bond the threaded lid to the jar).

Returning to FIG. 10, the optional cap 206 can provide additional protection for the wet packaged prosthetic heart valve 220, for example protecting the lid 204 from potential damage. The cap 206 can be formed from various materials that may or may not provide thermal insulation (e.g., the cap 206 can be silicon). Further, the cap 206 can be configured for assembly to the wet packaged prosthetic heart valve 220 (FIG. 11) in various manners (e.g., the cap 206 can be press fitted onto the cup 202, can be threaded to the cup 202, etc.). In some embodiments, the cap 206 can include or form a port 230. The port 230 can, for example, be sized and located to facilitate removal of liquid from the wet packaged prosthetic valve 220 via a syringe (not shown). Thus, the location of the port 230 can vary depending upon the orientation of the prosthetic heart valve 30 and its leaflets within the cup 202.

Figure 12:
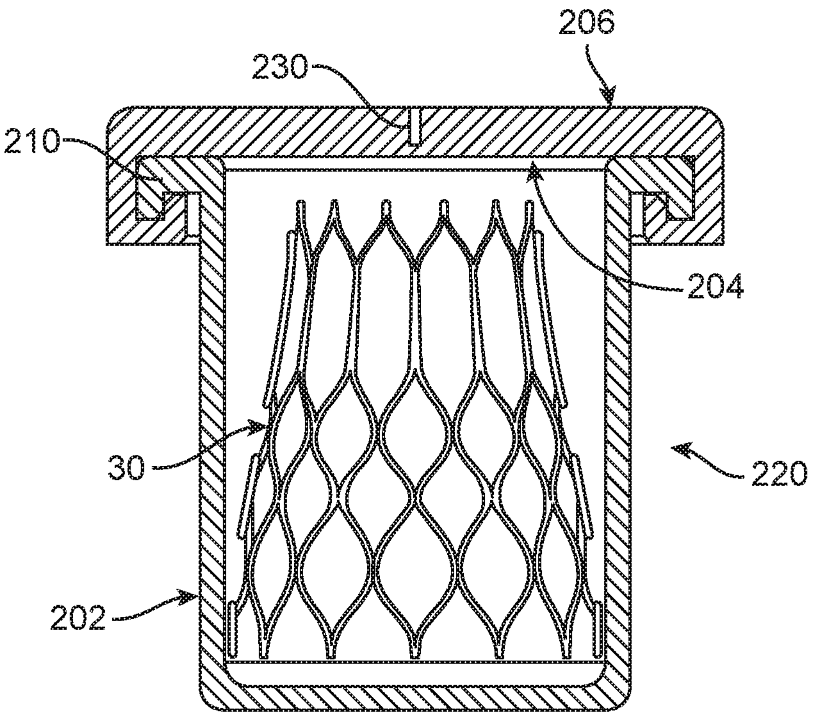
FIG. 12 is a cross-sectional view of the packaging system and prosthetic heart valve of FIG. 10 upon final assembly.

One example of the cap 206 assembled to the wet packaged prosthetic heart valve 220 is shown in FIG. 12. The cap 206 has been pressed fitted over, and in to engagement with, the rim 210, thereby covering the lid 204. In some embodiments, however, the cap 206 is unnecessary for establishing a complete, hermetically sealed environment between the lid 204 and the cup 202. As described above, the port 230 is located and arranged to facilitate access to the lid 204 by a syringe (not shown); with these and related embodiments, a user can drain liquid from the wet packaged prosthetic heart valve 220 without first disassembling the cap 206.

By sizing the cup 202 to more closes match a shape and size of the prosthetic heart valve 30, the packaging system 200 of FIG. 10 allows for reduced material, transportation and sterilization costs as compared to conventional wet packaged prosthetic heart valve designs. It reduces the amount of sterilization solution required to maintain the prosthetic heart valve 30 in a wet environment, thus improving end user experiences and reducing the environmental impact as compared to conventional designs. Further, the use of the flexible, peelable lid 204 eliminates issues with opening a conventional glass jar/threaded lid package. In some embodiments, the wet packaged prosthetic heart valve 220, with or without the cap 206, can be shipped in conventional secondary packaging and/or delivered within the vacuum flask 44 (FIG. 1) and cap 26 (FIG. 1) as described above.

Figure 13A:
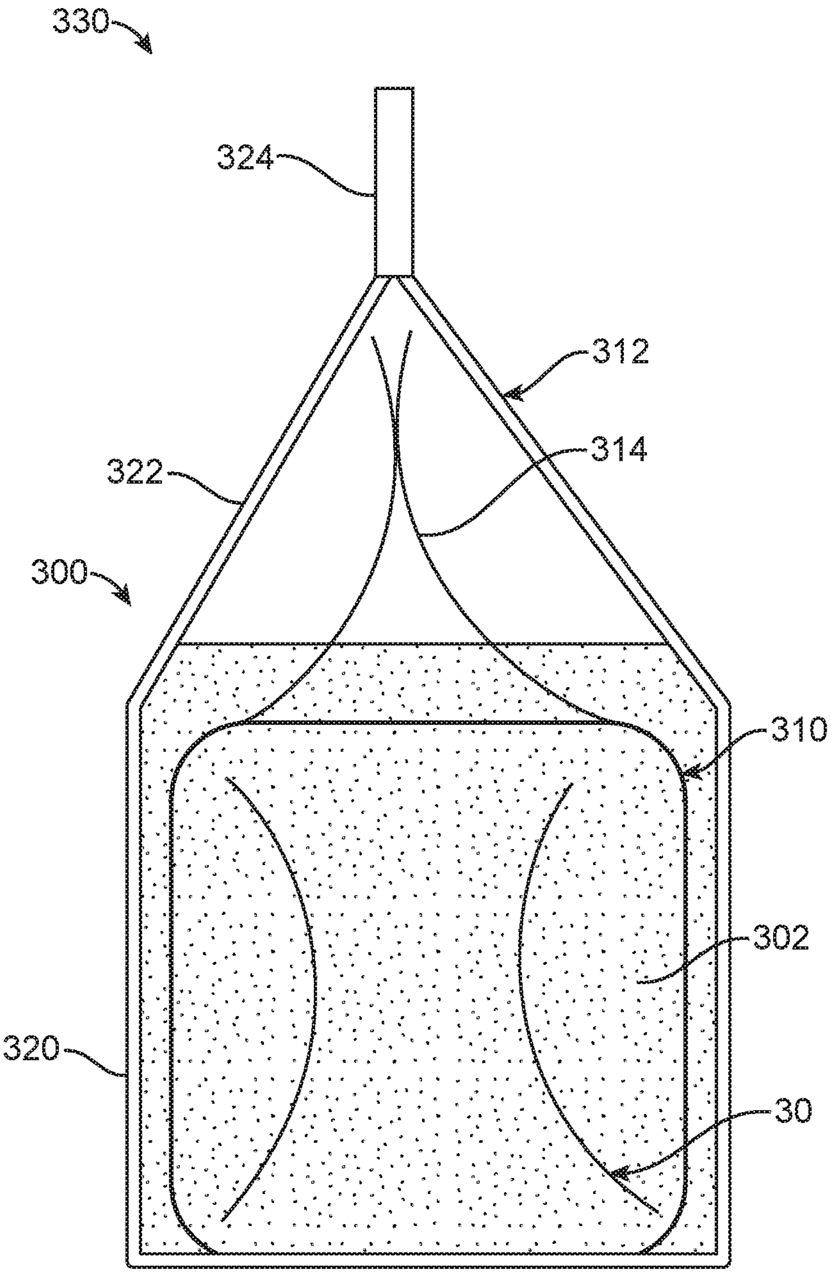
FIG. 13A is a simplified cross-sectional view of another packaging system in accordance with principles of the present disclosure containing a prosthetic heart valve and sterilization solution.
Figure 13B:
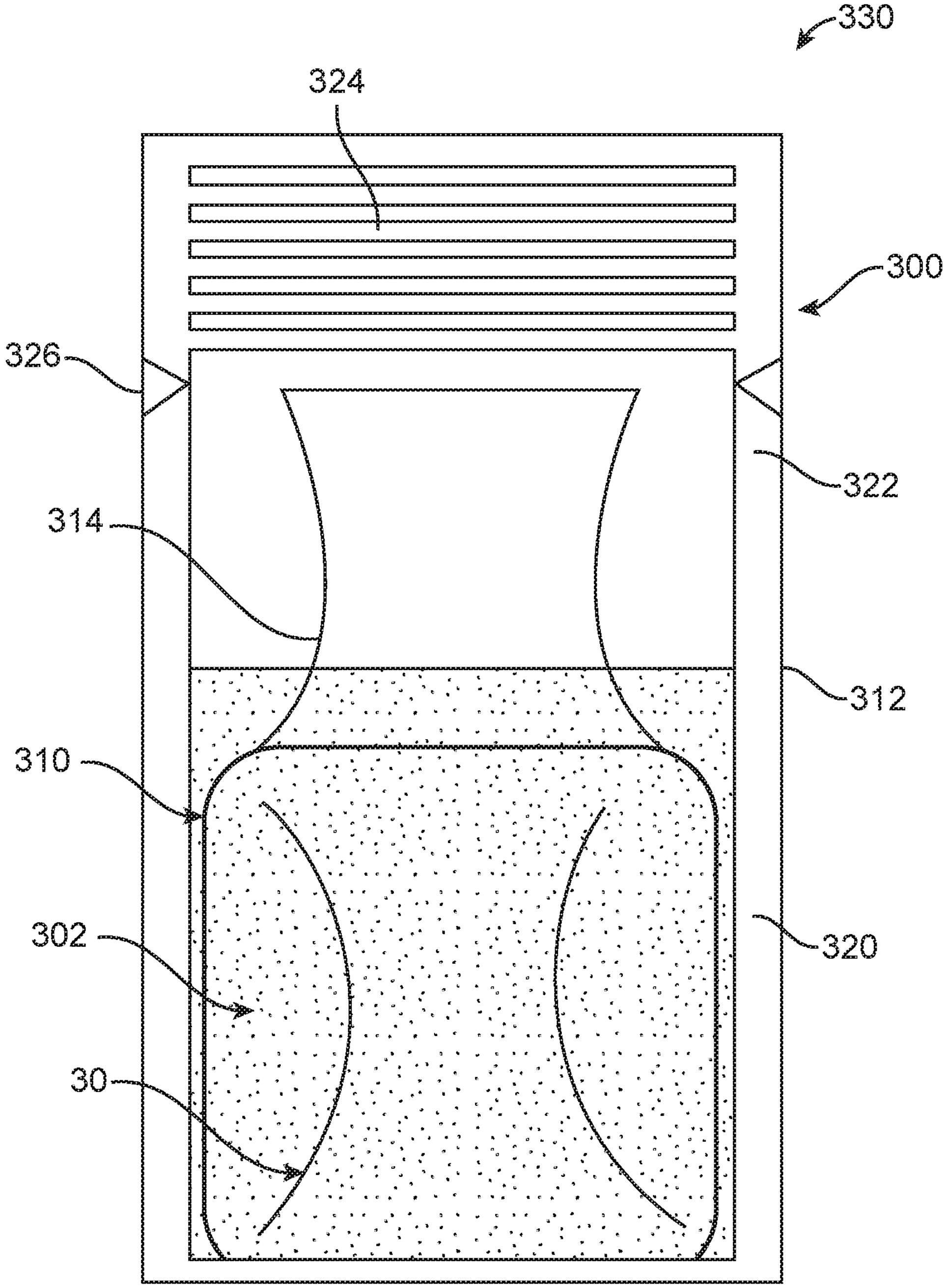
FIG. 13B is a cross-sectional view of the assembly of FIG. 13A taken along a plane ninety degrees to the plane of FIG. 13A.

Another embodiment of a packaging system 300 for storage and/or shipping of the prosthetic heart valve 30 maintained within a sterilization solution 302 (e.g., glutaraldehyde) in accordance with principles of the present disclosure is shown in FIGS. 13A and 13B. The packaging system 300 includes a frame 310 and a pouch 312. The frame 310 is configured to provide structural stability for the prosthetic heart valve 30, surrounding and protecting the prosthetic heart valve 30 from physical damage. The frame 310 is porous to readily permit ingress of the sterilization solution 302 into an interior of the frame 310, thus interacting with (including submerging) the prosthetic heart valve 30. Thus, for example, the frame 310 can be a wire mesh, a skeleton-type body, a porous material, etc. Regardless, the frame 310 is formed of a material that is compatible with the prosthetic heart valve 30 and the sterilization solution 302 (e.g., plastic). In some embodiments, the frame 310 can include or be provided with a handle 314 for convenient grasping by a user to remove the frame 310 (and thus the prosthetic heart valve 30 as carried by the frame 310) from the pouch 312. In some embodiments, and for reasons made clear below, the handle 314 can be foldable.

The pouch 312 is formed of a flexible material (e.g., foil or plastic film) that provides a sterile environment (e.g., a material of the pouch 312 is selected to be impervious to liquid and oxygen). The pouch 312 is sized and shaped in accordance with the frame 310, and thus the prosthetic heart valve 30. For example, the pouch 312 can be formed to provide or define a containment portion 320 and a leading portion 322. The containment portion 320 is sized and shaped to receive the prosthetic heart valve 30 (as carried within the frame 310) along with a sufficient volume of the sterilization solution 302 (e.g., the contained volume of the sterilization solution 302 is sufficient to fully submerge the prosthetic heart valve 30). The leading portion 322 extends from the containment portion 320, tapering in at least one outer dimension to an end region 324. Walls of the pouch 312 are sealed to one another at the end region 324, thereby forming a sterile, sealed environment for the contained prosthetic heart valve 30/sterilization solution 302. In some embodiments, features can be provided or formed that facilitate opening of the pouch 312 by a user. Notches, nicks or the like 326 can be partially formed through a thickness of a wall of the pouch 312 appropriate for tear initiation by a user as will be understood by one of ordinary skill, for example along the leading portion 322 at a location vertically above (relative to the orientation of FIGS. 13A and 13B) an expected fill line of the sterilization solution 302. With this but one acceptable configuration, a user can tear the pouch at the tear lines 326 to access the frame 310 (and thus the prosthetic heart valve 30 carried by the frame 310) without spilling the sterilization solution.

The packaging system 300 combines with the prosthetic heart valve 30 and the sterilization solution to provide or define a wet packaged prosthetic heart valve 330. The wet packaged prosthetic heart valve 330 can be delivered or shipped to an end user in various manners. In some non-limiting examples, the leading portion 322 can be folded (thus folding the handle 314) onto itself, and then the wet packaged prosthetic heart valve can be wrapped in insulation to protect from extreme temperatures and placed in a carton for shipping. As compared to conventional wet packaged prosthetic heart valve designs, the packaging system 300 uses less material, is lighter, and occupies less space (e.g., when the pouch 312 is folded). Further, opening of the pouch 312 by an end user is simple and straightforward, and is not negatively affected by the presence of glutaraldehyde. The prosthetic heart valve 30 can be easily removed from the pouch 312, and the sterilization solution 302 can conveniently be poured from the pouch 312 once the prosthetic heart valve 30 is removed. Moreover, the frame 310 and the liquid/sterilization solution 302 within the pouch 312 serve to protect the prosthetic heart valve 30 (e.g., the combination sterilization solution 302 and the pouch 312 act as a natural dampener).

Figure 14:
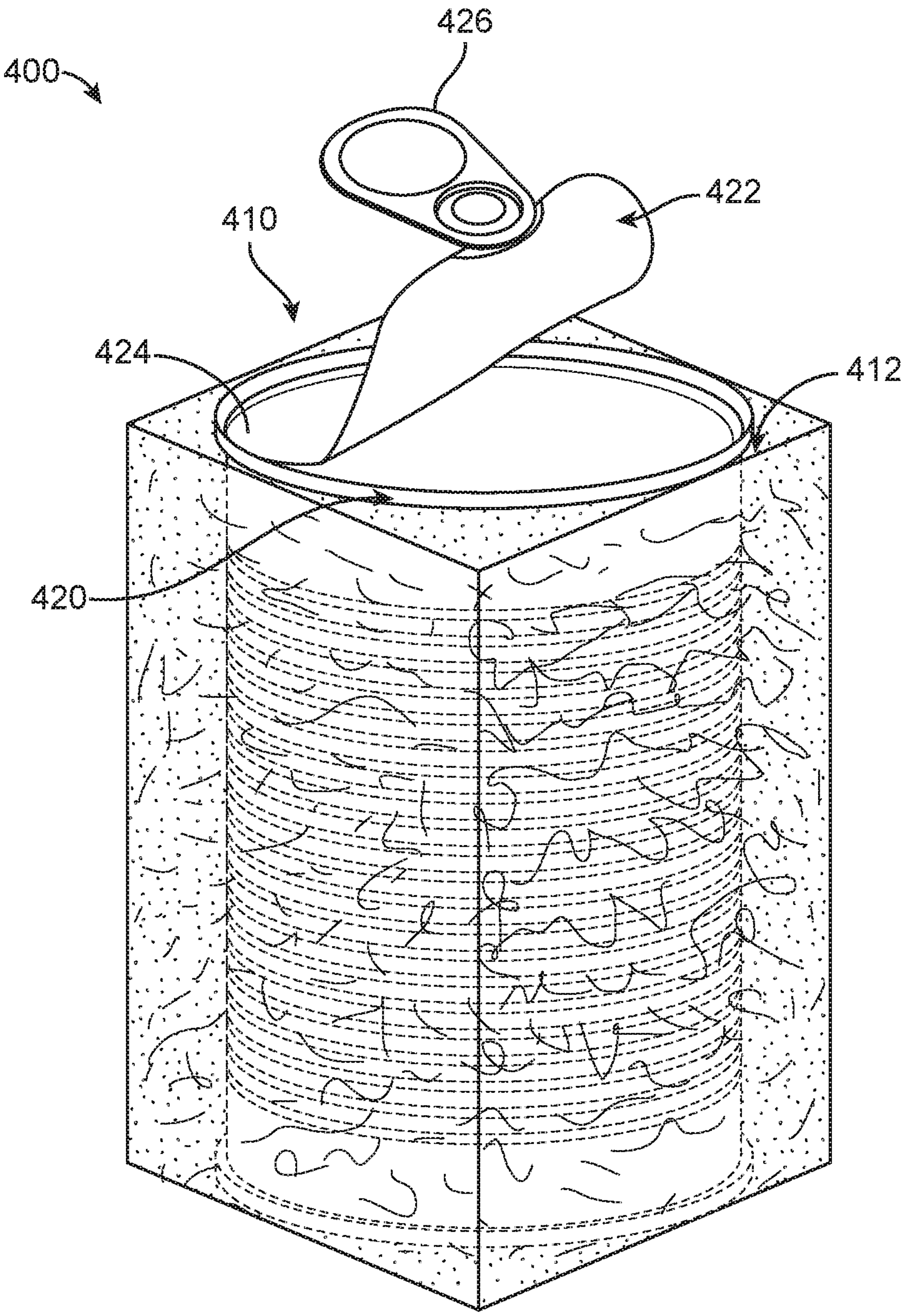
FIG. 14 is a perspective view of another packaging system in accordance with principles of the present disclosure.

Another embodiment of a packaging system 400 for storage and/or shipping of the prosthetic heart valve maintained within a sterilization solution (e.g., glutaraldehyde) in accordance with principles of the present disclosure is shown in FIG. 14. The packaging system 400 includes a container assembly 410 (referenced generally) and an insulator body 412. The container assembly 410 can be akin to steel or tin can packaging commonly used for consumable products such as soup, and includes a can or cup 420 and a lid 422. The can 420 is sized and shaped to receive and maintain the prosthetic heart valve (hidden) and appropriate volume of the sterilization solution. In some embodiments, the can 420 is formed of a thin metal (tin-plated steel, tin-free steel, tin, aluminum, etc.). The lid 422 is provided as part of a top end wall joined to the can 420 that includes a score line 424 (referenced generally). Optionally, a pull tab 426 can be provided with the lid 422. Prior to opening the lid 422, the container assembly 420 provide a sealed, sterile environment for the prosthetic heart valve and sterilization solution (e.g., prior to opening, the sealed container assembly 410 is impervious to liquid and oxygen). The container assembly 410 combines with the prosthetic heart valve and the sterilization solution to define or provide a wet packaged prosthetic heart valve. As understood by virtually all users, the lid 422 is easily opened, for example by applying a pulling force onto the pull tab 426, thus separating the lid 422 from the can 420 along the score line 424. The presence of the sterilization solution does not affect the ease with which the lid 422 can be removed. As compared to conventional wet prosthetic heart valve packaging, the container assembly 410 is designed for ease of use and is globally used in other industries without issue.

Figure 15:
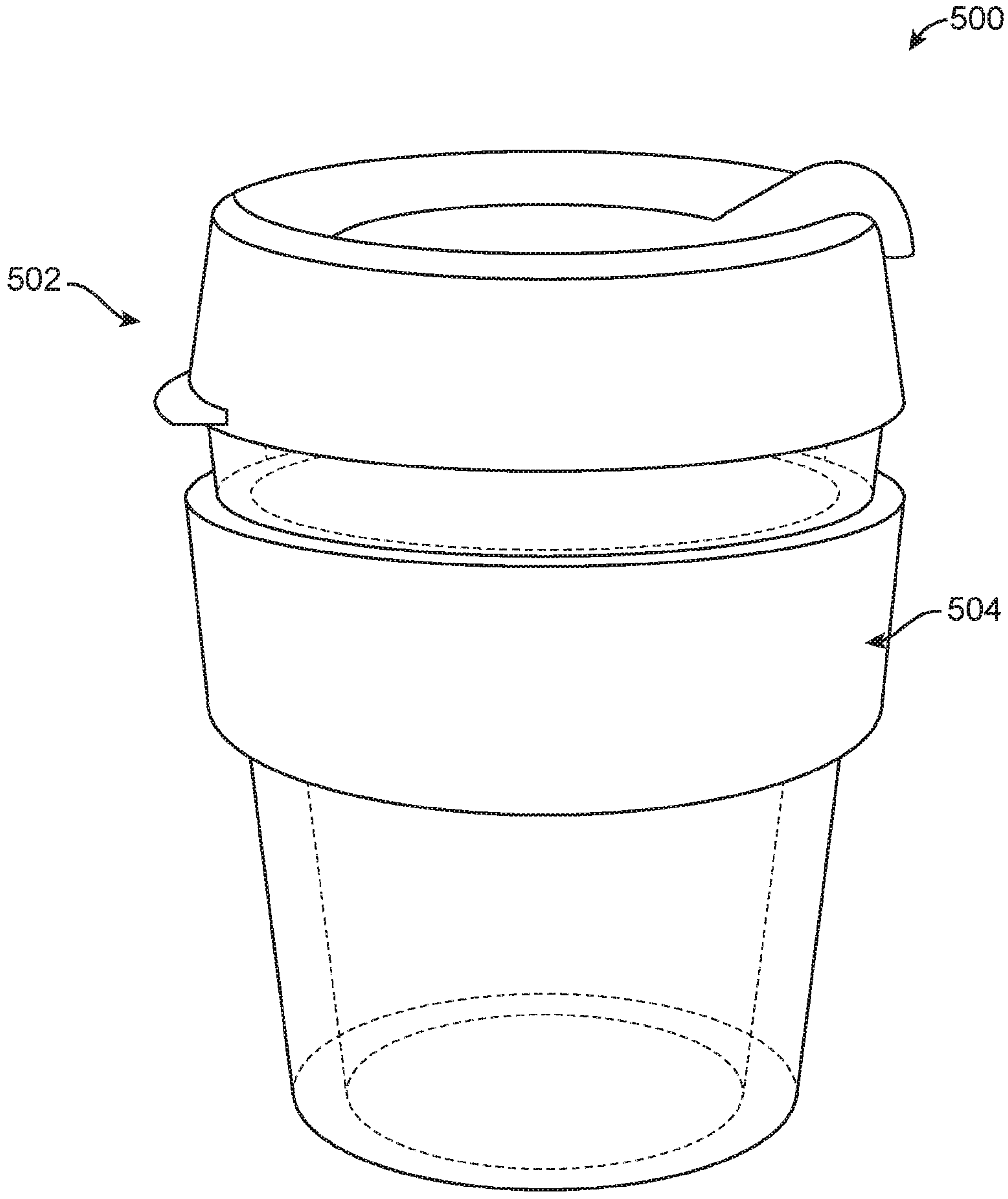
FIG. 15 is a side view of another packaging system in accordance with principles of the present disclosure

The insulator body 412 can assume various forms, appropriate for providing thermal insulation to the wet packaged prosthetic heart valve. For example, the insulator body 412 can define an interior open volume sized and shaped to receive can 420, and an exterior geometry conducive to shipping and storage (e.g., the insulator body 412 can have or form flat exterior surfaces as shown). A variety of materials are available that provide thermal insulation. In some non-limiting examples, the insulator body 412 is or includes a cork or cork-like material. With these and related embodiments, the cork material can improve recyclability of the packaging system 400 as compared to conventional designs. Other formats are also acceptable. For example, FIG. 15 illustrates another packaging system 500 in accordance with principles of the present disclosure that includes a container assembly 502 (referenced generally) and an insulator body 504. With the embodiment of FIG. 15, the insulator body 504 (e.g., cork or cork-like material) is provided as a sleeve that is fitted around the container assembly 502.

The packaging systems of the present disclosure provide a marked improvement over previous designs. For example, wet packaged prosthetic heart valves are provided that are easy to open, and not susceptible to possible interference by the presence of crystalized glutaraldehyde or other sterilization solutions. Further, some embodiments provide enhance thermal and physical protection, eliminating the need for expensive, additional packaging.

Although the present disclosure has been described with reference to preferred embodiments, workers skilled in the art will recognize that changes can be made in form and detail without departing from the spirit and scope of the present disclosure.

What is claimed is:

1. A packaging system storing a prosthetic heart valve in a volume of sterilization solution, the packaging system comprising:
- a cup comprising an interior region containing the prosthetic heart valve and the volume of sterilization solution, wherein the prosthetic heart valve is unconstrained within the interior region of the cup; and
- a lid;
- wherein the lid is securable to the cup to provide a hermetically sealed, sterile barrier to the interior region of the cup;
- and further wherein securement of the lid to the cup is characterized by the absence of a threaded interface between the lid and the cup, wherein the lid is a thin foil or film that is heat sealable to the cup.

2. The packaging system of claim 1, wherein the lid is configured to be removed from the cup by peeling the lid away from the cup.

3. The packaging system of claim 1, further comprising:
- a flask sized to receive the cup containing the prosthetic heart valve; and
- a cap configured for securement over an open end of the flask.

4. The packaging system of claim 3, further comprising:
- a temperature indicator device including a temperature sensor.

5. The packaging system of claim 4, wherein the temperature indicator device includes a display visible from an exterior of the cap and configured to convey information from the temperature sensor indicative of temperature conditions experience by the prosthetic heart valve over time.

6. The packaging system of claim 4, wherein the temperature indicator device includes a data logger configured to record temperature information from the temperature sensor over time.

7. A wet packaged prosthetic heart valve comprising:
- a cup;
- a prosthetic heart valve contained in an interior region of the cup, wherein the prosthetic heart valve is unconstrained within the interior region of the cup;
- a volume of sterilization solution contained in the interior region of the cup; and
- a lid heat sealed to a rim of the cup to provide a hermetically sealed, sterile barrier to the interior region of the cup.

8. The wet packaged prosthetic heart valve of claim 7, wherein the lid is a thin foil or film.

9. The wet packaged prosthetic heat valve of claim 7, wherein the lid is peelable from the rim.

10. A packaging system storing a prosthetic heart valve in a volume of sterilization solution, the packaging system comprising:
- a wet packaged prosthetic heart valve comprising a cup comprising an interior region containing the prosthetic heart valve and the volume of sterilization solution, and a lid secured to the cup to provide a hermetically sealed, sterile barrier to the interior region of the cup;
- a flask sized to receive the wet packaged prosthetic heart valve;
- a cap configured for fluid-tight securement over an open end of the flask, wherein the wet packaged prosthetic heart valve is configured to be received within a vacuum chamber defined by the flask and the cap; and
- a temperature indicator device configured to convey temperature information to a location exterior of the cap and the flask that is indicative of temperature conditions of the prosthetic heart valve of the wet packaged prosthetic heart valve when the wet packaged prosthetic heart valve is received within the vacuum chamber defined by the flask and the cap.

11. The packaging system of claim 10, wherein the temperature indicator device includes a data logger configured to record temperature information indicative of temperature conditions of the prosthetic heart valve of the wet packaged prosthetic heart valve over time.

12. The packaging system of claim 10, wherein the temperature indicator device comprises a viewing port and/or indicia configured to convey temperature information to the location exterior of the cap and the flask that is indicative of temperature conditions of the prosthetic heart valve of the wet packaged prosthetic heart valve when the wet packaged prosthetic heart valve is received within the vacuum chamber defined by the flask and the cap.

13. The packaging system of claim 10, wherein the temperature indicator device comprises a chemical temperature sensor.

14. The packaging system of claim 10, wherein the temperature indicator device is located directly on the wet packaged prosthetic heart valve.

15. The packaging system of claim 14, wherein the temperature sensor is applied to the lid of the wet packaged prosthetic heart valve.

16. The packaging system of claim 15, wherein the temperature indicator device further comprises a light guide configured to transmit light from the temperature sensor to the location exterior of the cap and the flask that is indicative of temperature conditions of the prosthetic heart valve of the wet packaged prosthetic heart valve when the wet packaged prosthetic heart valve is received within the vacuum chamber defined by the flask and the cap.

17. The packaging system of claim 16, wherein the cap further comprises a viewing port, and the light guide is configured to transmit the light through the viewing port when transmitting light from the temperature sensor to the location exterior of the cap and the flask.

18. The packaging system of claim 10, wherein the temperature indicator device further comprises a light guide configured to transmit light from the temperature sensor to the location exterior of the cap and the flask that is indicative of temperature conditions of the prosthetic heart valve of the wet packaged prosthetic heart valve when the wet packaged prosthetic heart valve is received within the vacuum chamber defined by the flask and the cap.

19. The packaging system of claim 18, wherein the cap further comprises a viewing port, and the light guide is configured to transmit the light through the viewing port when transmitting light from the temperature sensor to the location exterior of the cap and the flask.

20. The packaging system of claim 10, wherein the lid comprises a thin foil or film.

21. The packaging system of claim 20, wherein the thin foil or film is heat sealable to the cup.

* * * * *